United States Patent
Jung et al.

(10) Patent No.: US 7,196,178 B2
(45) Date of Patent: Mar. 27, 2007

(54) SUGAR-DERIVED GELLANT FOR HYDROGEL FORMATION

(75) Inventors: Jong Hwa Jung, Tsukuba (JP); George John, Tsukuba (JP); Toshimi Shimizu, Tsukuba (JP)

(73) Assignees: Japan Science and Technology Agency, Saitama (JP); National Institute of Advancco Industrial Science and Technology, Tokyo (JP)

( * ) Notice: Subject to any disclaimer, the term of this patent is extended or adjusted under 35 U.S.C. 154(b) by 0 days.

(21) Appl. No.: 10/415,729

(22) PCT Filed: Mar. 15, 2002

(86) PCT No.: PCT/JP02/02463

§ 371 (c)(1),
(2), (4) Date: Apr. 30, 2003

(87) PCT Pub. No.: WO03/014249

PCT Pub. Date: Feb. 20, 2003

(65) Prior Publication Data

US 2004/0014683 A1   Jan. 22, 2004

(30) Foreign Application Priority Data

Aug. 7, 2001  (JP) ........................................ 2001-239014

(51) Int. Cl.
C07H 17/00 (2006.01)
C07H 1/00 (2006.01)
C07H 1/06 (2006.01)

(52) U.S. Cl. .................... 536/17.2; 536/18.7; 536/55.3; 536/124; 536/127

(58) Field of Classification Search ................ 536/17.2, 536/18.7, 55.3, 124, 127
See application file for complete search history.

(56) References Cited

U.S. PATENT DOCUMENTS

| 4,271,153 A | 6/1981 | Gauri |
| 4,882,316 A | 11/1989 | Lambert et al. |
| 5,405,987 A | 4/1995 | Elango et al. |
| 5,808,067 A | 9/1998 | Saukaitis et al. |

FOREIGN PATENT DOCUMENTS

| JP | 57/106696 | 7/1982 |
| JP | 8/325288 | 12/1996 |
| JP | 11/323309 | 11/1999 |
| JP | 2002/248258 | 9/2000 |

OTHER PUBLICATIONS

Murata et al., "Thermal and Light Control of the Sol–Gel Phase Transitin in Cholesterol–Based Organic Gels . . . ", J. Am. Chem. Soc., 1994, 116, 6664–6676.

Jeong et al., "Dual–component cholesterol–based gelators bearing complementary hydrogen–bonding sites", Supramolecular Science 3 (1996) 83–86.

Shinkai et al., "Cholesterol–based functiona tectons as versitile building–blocks for liquid crystals, organic gels and monolayers", J. Mater. Chem., 1998, 8 (3), 485–495.

(Continued)

*Primary Examiner*—James O. Wilson
*Assistant Examiner*—Everett White
(74) *Attorney, Agent, or Firm*—Gary C Cohn PLLC

(57) ABSTRACT

A gelatinizer having gel-forming capability in both organic solvents and water, is provided. The hydrogelatinizer is represented by:

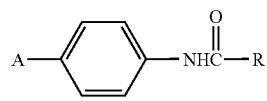

(where, A is a sugar residue, and R is an alkyl group).

12 Claims, 3 Drawing Sheets

OTHER PUBLICATIONS

Yoza et al., "Sugar–Integrated Gelators of Organic Solvents—Their Remarkable Diversity in Gelation Ability and Aggregate Structure", Chem. Eur. J. 1999, 5, 2722–2729.

Wang et al., "Direct Observation of Sol–Gel Conversion: The Role of the Solvent in Organogel Formation", J. Am. Chem. Soc, 2000, 122, 2399–2400.

Duncan et al., "1H NMR Investigation of the Composition, Structure, and Dynamics of Cholesterol–Stilbene Tethered Dyad Organogels", Langmuir 2000, 16, 6445–6452.

Geiger et al., "Organogels Resulting from Competing Self–Assembly Units in the Gelator . . . ", Langmuir 1999, 15, 2241–2245.

Terech et al., "Low Molecular Mass of Organic Liquids and the Properties of Their Gels", Chem. Rev. 1997, 97, 3133–3159.

Ostuni et al., "Novel X–ray Method for In Situ Determination of Gelator Strand Structure: Polymorphism . . . ", Angew. Chem. Int. Ed. Engl 1996, 35 (12) 1324–1326.

Terech et al., "Structures of Organogels Based upon Cholesteryl 4–(2–Anthryloxy)butanoate . . . ", J. Phys. Chem, 1995, 99, 9558–9566.

Abdallah et al., "Organogels and Low Molecular Mass Organic Gelators", Adv. Mater. 2000, 12, 1237–1247.

Hanabusa et al., "Prominent Gelation and Chiral Aggregation of Alkylamides Derived from trans–1,2–Diaminocyclohexane", Angew. Chem. Int. Ed. Engl. 1996, 35 (17), 1949–1951.

De Loos et al., "Remarkable Stabilization of Self–Assembled Organogels by Polymerization", J. Am. Chem. Soc. 1997, 119, 12675–12676.

Schoonbeek et al., "Geminal Bis–ureas as Gelators for Organic Solvents: Gelation Properties and Structural Studies in Solution and the Gel State", Chem Eur. J. 2000, 6 (14), 2633–2643.

Carr et al., "The Design of Organic Gelators: Solution and Solid State Properties of a Family of Bis–Ureas", Tetrahedron Letters 39 (1998) 7447–7450.

Shi et al.,, "The Gelation of CO2: A Sustainable Route to the Creation of Microcellular Materials", Science 289 (1999) 1540–1544.

Fuhrhop et al., "The Chiral Bilayer Effect Stabilizes Micellar Fibers", J. Am Chem. Soc. 1987, 109, 3387–3390.

Fuhrhop et al., Stereochemistry and Curvature Effects in Supramolecular Organization and Separation Processes of Micellular N–Alkylaldonamide Mixtures, J. Am Chem. Soc. 1990, 112, 1768–1776.

Yoza et al., "Sugar–integrated gelators of organic fluids: on their versatility as building–blocks and diversity in superstructures", Chem Commun. 1998, 907–908.

Menger et al., "Anatomy of a Gel. Amino Acid Derivatives that Rigidify Water and Submillimolar Concentration", J. Am. Chem. Soc., 2000, 122, 11679–11691.

Hanabusa et al., "Formation of physical hydrogels with terpyridine–containing carboxylic acids", Colloids and Surfaces A: Physicochemical and Engineering Aspects 169 (2000) 307–315.

John et al., "Nanotube Formation from Renewable Resources via Coiled Nanofibers", Adv. Mater. 2001, 13 (10) 715–718.

Masuda et al., "Polymerization in Nanometer–Sized Fibers: Molecular Packing Order and Polymerizability", Macromolecules 2000, 33, 9233–9238.

Nakazawa et al., Spontaneous Formation of Helically Twisted Fibers from 2–Glucosamide Bolaamphiphiles . . . : Langmuir 1999, 15, 4757–4764.

Shimizu et al., "Stereochemical Effect of Even–Odd Connecting Links on Supramolecular Assemblies Made of 1–Glucosamide Bolaamphiphiles", J. Am. Chem. Soc. 1997. 119. 2812–2818.

Van Esch et al., "New Functional Materials Based on Self–Assembling Organogels: From Serendipity towards Design", Angew. Chem. Int. Ed. 2000, 39 (13) 2263–2266.

James et al., "Chiral Discrimination of Monosaccharides through Gel Formation", Chemistry Letters (1994) 273–276.

Estroff et al., "Effective Gelation of Water Using a Series of Bis–urea Dicarboxylic Acids", Angew. Chem. Int. Ed. 2000, 39, 3447–3450.

SUGAR-DERIVED GELLANT FOR HYDROGEL FORMATION

FIELD OF THE INVENTION

This invention relates to a gelatinizer having a gel-forming ability regarding both organic solvents and water.

PRIOR ART

In recent years, in the field of super high polymer chemistry, the formation of desired high-order structures from monomers is being intensively studied. Much attention is being given to the development of small molecule gelatinizers which can be used on both a microscopic and macroscopic scale, which are industrially effective over a wide range of fields such as, for example, foodstuffs, deodorants, cosmetics, cushioning for running shoes or chromatography, and which easily lend themselves to manufacture (Murata, K.; Aoki, M.; Suzuki, T.; Harada, T.; Kawabata, H.; Komori, T.; Ohseto, F.; Ueda, K.; Shinkai, S. J. Am. Chem. Soc. 1994, 116, 6664 and references therein.: James, T. D.; Murata, K.; Harada, T.; Ueda, K.; Shinkai, S. Chem. Lett. 1994, 273.: Jeong, S. W.; Murata, K.; Shinkai, S. Supramol. Sci. 1996, 3, 83;: Shinkai, S.; Murata, K. J. Mater. Chem. (Feature Article) 1998, 8, 485.: Yoza, K.; Amanokura, N.; Ono, Y.; Akao, T.; Shinmori, H.; Takeuchi, M.; Shinkai, S.; Reinhout, D. L. Chem. Eur. J. 1999, 5, 2722: Wang, R.; Geiger, C.; Chen, L.; Swanson, B.;•Whitten, D. G. J. Am. Chem. Soc. 2000, 122, 2399.: Duncan, D. C.; Whitten, D. G. Langmuir 2000, 16, 6445.: Geiger, C.; Stanescu, M.; Chen, L.; Whitten, D. G. Langmuir 1999, 15, 2241.: Terech, P.; Weiss, R. G. Chem. Rev. 1997, 3313.: Otsuni, E.; Kamaras, P.; Weiss, R. G. Angew. Chem., Int. Ed. 1996, 35, 1324 and references therein.: Terech, P.; Furman, I.; Weiss, R. G. J. Phy. Chem. 1995, 99, 9558 and references therein.: Abdallach, D. J.; Weiss, R. G. Adv. Mater. 2000, 12, 1237.: Hanabusa, K.; Yamada, M.; Kimura, M.; Shirai, H. Angew. Chem. Int. Ed. 1996, 35, 1949.: Loos, M.; Esch, J. v.; Stokroos, I.; Kellogg, R. M.; Feringa, B. L. J. Am. Chem. Soc. 1997, 119, 12675.: Schoonbeek, F. S.; Esch, J. v.; Hulst, R.; Kellogg, R. M.; Feringa, B. L. Chem. Eur. J. 2000, 6, 2633.: Esch, J. v.; Feringa, B. L. Angew. Chem., Int. Ed. 2000, 39, 2263.: Melendez, R.; Geib, S. J.; Hamilton, A. D. Molecular AutoAssembly Organic Versus Inorganic Approaches, Fujita, M., Ed.; Springer, 2000.: Carr, A. J.; Melendez, R.; Geib, S. J.; Hamilton, A. D. Tetrahedron Lett. 1998, 39, 7447.: Shi, C.; Kilic, S.; Xu, J.; Enick, R. M.; Beckman, E. J.; Carr, A. J.; Melendez, R. E.; Hamilton, A. D. Science 1999, 286, 1540.).

By observing the SEM and TEM of these gelatinizers, it has been found that low molecular weight fibrous agglomerates formed by non-covalent bond interactions cause this gelating effect. "Aqueous gels" are normally manufactured from macromolecules such as proteins or polymers, and unlike "organic gels" having reversible high-order structures which are one-dimensional agglomerates of low molecular weight formed by autocoagulation, it is difficult to identify this complex interaction. However, a small number of "aqueous gels" comprising agglomerates of low molecular weight compounds do exist (Estroff, L. A.; Hamilton, A. D. Angew. Chem. Int. Ed. 2000, 39, 3447.: Fuhrhop, J.-H.; Schnieder, P.; Rosenbery, J.; Boekema, E. J. Am. Chem. Soc. 1987, 109, 3387.: Fuhrhop, J.-H.; Boettcher, C. J. Am. Chem. Soc. 1990, 112, 1768.: Yoza, K.; Ono, Y.; Yoshihara, K.; Akao, T.; Shinmori, H.; Takeuchi, M.; Shinkai, S.; Reinhout, D. L. Chem. Commun. 1998, 907.: Menger, F.; Caran, K. J. Am. Chem. Soc. 2000, 122, 11679.: Hanbusa, K.; Hirata, T.; Inoue, D.; Kimura, M.; Touhara, H.; Shirai, H. Colloid. Sur., A. 2000, 169, 387.).

PROBLEMS WHICH THIS INVENTION AIMS TO SOLVE

As far as the Inventors are aware, the microscopic structure of aqueous gels has not yet been clarified in detail by measurement techniques such as NMR and X-rays. The Inventors focused their attention on developing novel agglomerates derived from sugars which could be formed in water (John, G.; Masuda, M.; Okada, Y.; Yase, K.; Shimizu, T. Adv. Mater. 2001, 13, 715.: Masuda, M.; Hanada, T.; Okada, Y.; Yase, K.; Shimizu, T. Macromolecules 2000, 33, 9233.: Nakazawa, I.; Masuda, M.; Okada, Y.; Hanada, T.; Yase, K.; Asai, M.; Shimizu, T. Langmuir 1999, 15, 4757.: Shimizu, T.; Masuda, M. J. Am. Chem. Soc. 1997, 119, 2812.).

The advantage of this system is that, by using the rich basic skeleton of the hydrocarbon family, various types of agglomerates can be systematically designed.

The Inventors designed several gelatinizers, and by performing this type of analysis, they carried out studies on gelatinizers which had excellent gel-forming abilities in both organic solvents and water.

MEANS TO SOLVE THE ABOVE PROBLEMS

The Inventors already discovered that a gelatinizer derived from glucose, gelatinizes water/alcohol (volume ratio=1:1) or water/acetone (volume ratio=1:1) (John, G.; Masuda, M.; Okada, Y.; Yase, K.; Shimizu, T. Adv. Mater. 2001, 13, 715.). This discovery suggested that if sugars were studied in more detail, as was the case for suitable hydrophobic groups, some novel aqueous gelatinizers might be found, and might be useful in specifying the basic structural criteria for designing aqueous gels. With this object in mind, we designed novel gelatinizers having a sugar part, an aminophenyl and a long-chain alkyl group.

As a result of these studies, the Inventors discovered that the hydrogelatinizer represented by the following chemical formula:

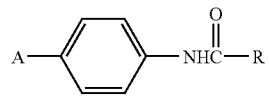

(where, A is a sugar residue and R is an alkyl group) had excellent gel-forming abilities in both organic solvents and water.

The long-chain alkyl group forming the end of this gelatinizer improves solubility in organic solvents, but at the same time it promotes aggregation of fibres due to Van der Waals forces, and finally forms a gel.

DETAILED DESCRIPTION OF THE INVENTION

Figure 1:
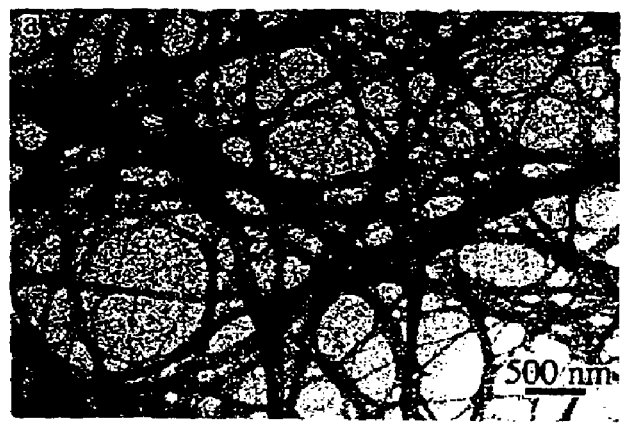
FIG. 1 shows an EF-TEM photograph of an aqueous gel manufactured using the gelatinizer of this invention.

This invention will now be described in more detail, but it should be understood that this description is not be construed as limiting the invention in any way.

The hydrogel of this invention is represented by:

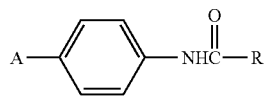

Here, A is a sugar residue. This sugar may be a monosaccharide, oligosaccharide or polysaccharide, but it is preferably a monosaccharide. Examples of this monosaccharide are hexoses such as glucose, galactose and N-acetylglucosamine, and pentoses such as L-arabinoside and xylose, but aldopyranose is preferred.

Pyranoses may be α or β. Examples of the aldopyranose are α-D-glucose, α-D-galactose, α-D-mannose, β-D-glucose, β-D-galactose, β-D-mannose, p-nitrophenyl-α-D-glucopyranoside, p-nitrophenyl-α-D-galactopyranoside, p-nitrophenyl-α-D-mannopyranoside, p-nitro phenyl-β-D-glucopyranoside, p-nitro phenyl-β-D-galactopyranoside and p-nitrophenyl-β-D-mannopyranoside. However, the aldopyranose is preferably glucopyranose or galactopyranose.

The residue is a residue obtained by removing the hydrogen atom from any of the hydroxyl groups of the sugar, and preferably, is a residue obtained by removing the hydrogen atom from any of the hydroxyl groups bonded to the six-member ring of aldopyranose.

R in the aforesaid chemical formula is an alkyl group. This alkyl group may be straight chain or branched, but straight chain is preferred. The number of carbon atoms is preferably 6–20, but more preferably 10–20.

The hydrogelatinizer of this invention can solidify a large amount of water with a small amount of solid gelatinizer, and due to its ability to function as a water retention agent (water retention agent for desert greenification or plant cultivation), as a water absorbent (pet tray urine absorber or physiological water absorber) and as an alcohol-retaining agent since it also solidifies small amounts of alcohol components, it can solidify fuel solids, organic solvents and oils. It may be used as a household oil caking agent, heavy oil solidifying agent or organic effluent solidifying agent, and as it is a flexible material containing a large amount of water, it has potential application as a biological compatibility material, tissue/cell culture matrix, or biological material separator of proteins and nucleic acids.

EXAMPLES

In the following examples, the gelatinizer of this invention was manufactured, and its agglomerating properties in water were analyzed by EF-TEM (transmission electron microscope with energy filter) (Nakazawa, I.; Masuda, M.; Okada, Y.; Hanada, T.; Yase, K.; Asai, M.; Shimizu, T. Langmuir 1999, 15, 4757.), NMR, FT-IR and XRD.

Example 1 p-nitrophenyl-β-D-glucopyranoside (Tokyo Chemical Industries) (250 mg) was dissolved in a methanol/tetrahydrofuran mixed solvent (20 ml/5 ml), and 10% palladium carbon (250 mg) was added to this solution. Hydrogen gas was introduced under a nitrogen gas atmosphere into the reaction solution at room temperature for 3 hours. The reaction mixture was filtered to remove palladium carbon, the filtrate was evaporated under vacuum, and solidified. This residue was purified by silica gel chromatography using a tetrahydrofuran/chloroform mixed solvent (1/1, volume ratio) as an eluant, and p-aminophenol-β-D-glucopyranoside was obtained.

Yield 80–90%; $^1$H-NMR (300MHz, DMSO-d6): δ=3.44–4.10 (m, 6H), 4.76 (s, 2H), 5.25–5.31 (m, 3H), 5.60 (s, 1H), 6.70 (d, J=9.0 Hz, 2H), 6.95 (d, J=9.0 Hz, 2H), 7.37–7.46 (m, 5H); FT-IR (KBr): ν=3312, 2909, 1635, 1510, 1364, 1217, 1089, 1005, 1035, 999, 806, 706 cm$^{-1}$; MS (NBA): m/z: 360 [M+H]$^+$; elemental analysis calcd (%) for $C_{19}H_{21}NO_6$: C 63.50, H 5.89, N 3.90; found: C 63.18, H 6.04, N 3.78.

The p-aminophenol-β-D-glucopyranoside (250 mg) thus obtained was dissolved in tetrahydrofuran (20 ml), and lauroyl chloride (300 mg) and triethylamine (1.0 g) were added. The reaction mixture was refluxed for 5 hours. The reaction solution was filtered to remove solids, and the filtrate was evaporated under vacuum to give a dry solid. The residue was purified by silica gel chromatography using a tetrahydrofuran/chloroform mixed solvent (1/1, volume ratio) as an eluant, and dodecanoylaminophenol-β-D-glucopyranoside was thus obtained.

Yield 80%; $^1$H-NMR (300 MHz, CDCl$_3$): δ=0.9 (t, 3H), 1.5–3.0 (m, 15H), 3.50–4.13 (m, 6H), 4.76 (s, 2H), 5.25–5.31 (m, 3H), 5.63 (s, 1H), 6.70 (d, J=9.0 Hz, 2H), 6.98 (d, J=9.0 Hz, 2H), 7.30 (d, 2H) ; FT-IR (KBr): ν=3340, 2912, 1630, 1510, 1364, 1217, 1089, 1005, 1035, 999, 806, 706 cm$^{-1}$; MS (NBA): m/z: 452.27 [M+H]$^+$; elemental analysis calcd (%) for $C_{24}H_{37}NO_7$: C 63.84, H 8.26, N 3.10; found: C 62.15, H 8.37, N 3.30

Example 2

An identical procedure was performed using p-nitrophenyl-β-D-galactopyranoside (Tokyo Chemical Industries) instead of p-nitrophenyl-β-D-glucopyranoside of Example 1, and p-aminophenyl-β-D-galactopyranoside was thus obtained.

Further, an identical procedure was performed using the p-aminophenyl-β-D-galactopyranoside obtained herein instead of the p-aminophenyl-β-D-glucopyranoside of Example 1, and dodecanoylaminophenol-β-D-galactopyranoside was thus obtained.

Yield 90%; $^1$H NMR (300 MHz, CDCl$_3$): δ=0.9 (t, 3H), 1.5–3.0 (m, 15H), 3.50–4.13 (m, 6H), 4.76 (s, 2H), 5.25–5.31 (m, 3H), 5.63 (s, 1H), 6.70 (d, J=9.0 Hz, 2H), 6.98 (d, J=9.0 Hz, 2H), 7.30 (d, 2H); FT-IR (KBr): ν=3340, 2912, 1630, 1510, 1364, 1217, 1089, 1005, 1035, 999, 806, 706 cm$^{-1}$; MS (NBA): m/z: 452.27 [M+H]$^+$; elemental analysis calcd (%) for $C_{24}H_{37}NO_7$: C 63.84, H 8.26, N 3.10; found: C 63.15, H 8.25, N 3.15.

The dodecanoylaminophenol-β-D-glucopyranoside and dodecanoylaminophenol-β-D-galactopyranoside (1 mg of each) obtained in the above experiments were respectively weighed out into test tubes, and a mixed solvent of water (900 mg) and methanol (100 mg) was added. The mixture was heated to ensure complete dissolution. Subsequently, it was gradually cooled, and left at room temperature for approximately 2–5 hours. A hydrated gel which did not collapse even when inverted, was obtained.

Gel-forming Ability Test Results

The gel-forming ability was evaluated as follows.

The solvent was water (including a small amount of methanol and ethanol), methanol, ethanol, 1-butanol, t-butanol, tetrahydrofuran, chloroform, dichloromethane, n-hexane, ethyl acetate, dimethylformamide or dimethyl sulfoxide.

One of the aforesaid solvents was mixed in a test tube wherein the two types of gelatinizer prepared in the Examples were sealed such that the concentration of gelatinizer was 0.1–3.0 wt %, and this mixture was heated until the solids dissolved. The resulting solution was cooled to 25° C. for one hour. The gelatinizer and solvent were introduced into a test tube capped by a diaphragm, and heated in the oil bath until the solids dissolved. This solution was cooled to 25° C.

At this stage, the formation of a stable gel was observed for the solvents 1-butanol, t-butanol, tetrahydrofuran, chloroform, dichloromethane, n-hexane, ethyl acetate, dimethylformamide, dimethyl sulfoxide and water, but it dissolved in the case of methanol and ethanol.

It is extremely interesting that water containing a small amount of alcohol (approximately 1 wt %, corresponding to 5000 or more molecules per molecule of gelatinizer), was gelated by the gelatinizer of this invention at a concentration of 0.1 wt % or less. These results show that the gelatinizer of this invention is an amphoteric gelatinizer agent which works on both water and organic solvents.

Figure 2:
FIG. 2 is an EF-TEM photograph of an aqueous gel manufactured using the gelatinizer of this invention, and is an enlargement of FIG. 1. The arrows shows spiral fibres.
Figure 3:
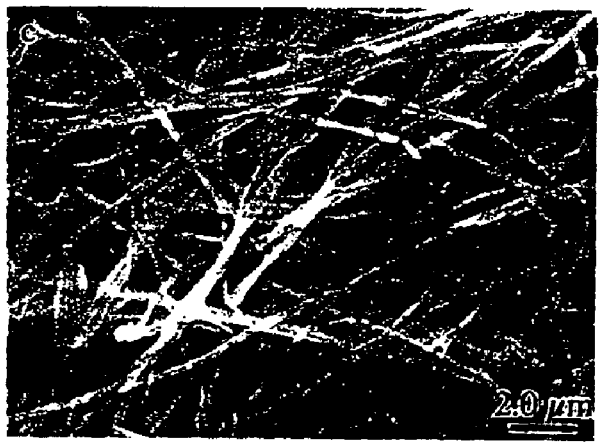
FIG. 3 is a diagram showing an SEM photograph of an aqueous gel manufactured using the gelatinizer of this invention.

FIGS. 1–3 show EF-TEM and SEM images of an aqueous gel produced by the gelatinizer of this invention for the purpose of visually observing chiral aggregation produced by the sugar part. FIG. 1 and FIG. 3 are typical photographs of an aqueous gel produced by the gelatinizer of this invention. These photographs clearly show that this gelatinizer is formed of a 3-dimensional network comprising creased fibres having a diameter of 20–500 nanometers. From the SEM photograph (FIG. 3), it is clear that several ribbon-shaped structures are twisted together to form a left-handed spiral. Further, from a TEM analysis of the chiral aggregate, it is seen that the fibres are twisted spiral ribbons having a width of approximately 85 nanometers, a pitch of approximately 315 nanometers and length of several micrometers, and that this is specifically left-handed (FIG. 2). These spiral aggregates explain how, instead of a crystal stable to heat, a quasi-stable gel is formed.

The $^1$H-NMR measurement results for the aqueous gel produced by the gelatinizer of this invention provide further proof that this aqueous gel is a self-aggregate. As shown on the left in FIG. 4, at 27° C., aromatic peaks are observed for the gel phase of the aggregate at 7.43 ppm (d, J=8.61 Hz, $H_b$ (for $H_b$, see chemical formula below) and 7.38 ppm (d, J=8.61 Hz, $H_a$ (for $H_a$, see chemical formula below)).

Figure 4:
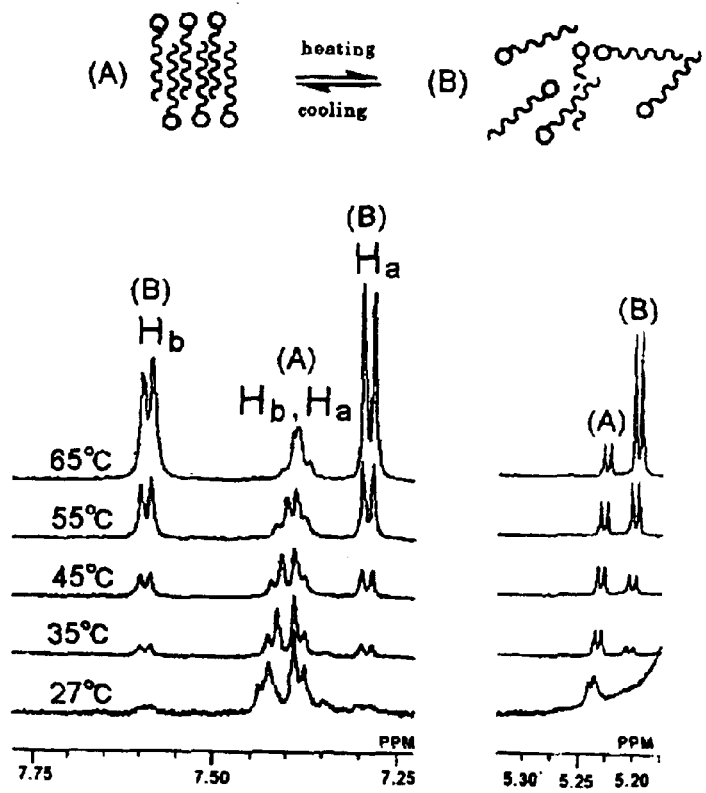
FIG. 4 is a $^1$H-NMR spectrum of an aqueous gel in $D_2O$ and methanol-$d_4$ (volume ratio=1:1).

Due to heating, new peaks eventually appear at 7.60 ppm (d, J=8.61 Hz, $H_b$) and 7.28 ppm (d, J=8.61 Hz, $H_a$), and the peaks at 7.43 ppm and 7.38 ppm disappear. The difference in the chemical shifts of the aromatic protons $H_a$, $H_b$ is probably due to π—π stacking and hydrogen bonding. This can be explained in view of the fact that the induction effect of the hydrogen bond is too large, and the shift of $H_a$ (to higher field) due to π—π stacking interactions cannot be cancelled out. An identical phenomenon was observed in the aromatic proton at the C-1 position of the sugar part (FIG. 4, right). The fact that different spectra were observed for aggregates and non-aggregates shows that chemical substitution is slower than the time scale of NMR. This is the first time stabilization of an aggregate by hydrogen bonding and π—π stacking interactions in the gel phase have been observed on a $^1$H-NMR spectrum, and strongly supports the idea that aromatic units lead to increased structural strength and assist the formation of the aqueous gel. As it is extremely difficult and almost impossible to obtain useful information regarding intramolecular hydrogen bonding in an aqueous gel from FT-IR observations, the Inventors obtained proof of intramolecular hydrogen bonding in a $D_2O$ system. The FT-IR spectrum of the aqueous gel incorporating deuterium is characterized by absorption bands at 1645 cm$^{-1}$ (—C=O, amide 1) and 1514 cm$^{-1}$ (—NH, amide II). Further, IR bands were observed at 3398 cm$^{-1}$ (—OH), 3298 cm$^{-1}$ (—NH) and 1658 cm$^{-1}$ (—C=O) with identical results in a cyclohexane gel. These results show that the amide groups in the aqueous gel not only form intramolecular hydrogen bonds in the gel phase, but confer a stronger hydrogen bonding effect than in a cyclohexane gel.

Figure 5:
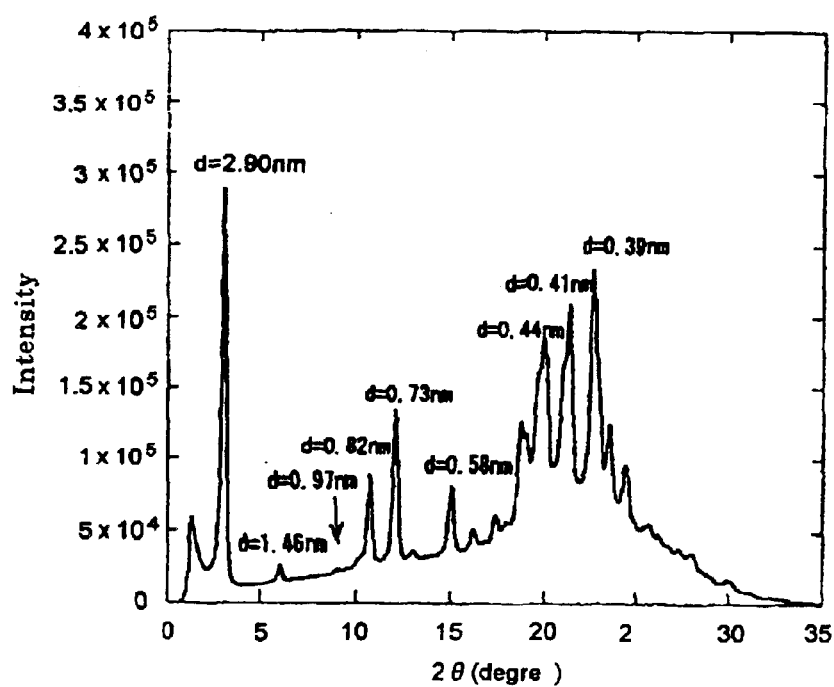
FIG. 5 is an XRD spectrum of a xerogel.
Figure 6:
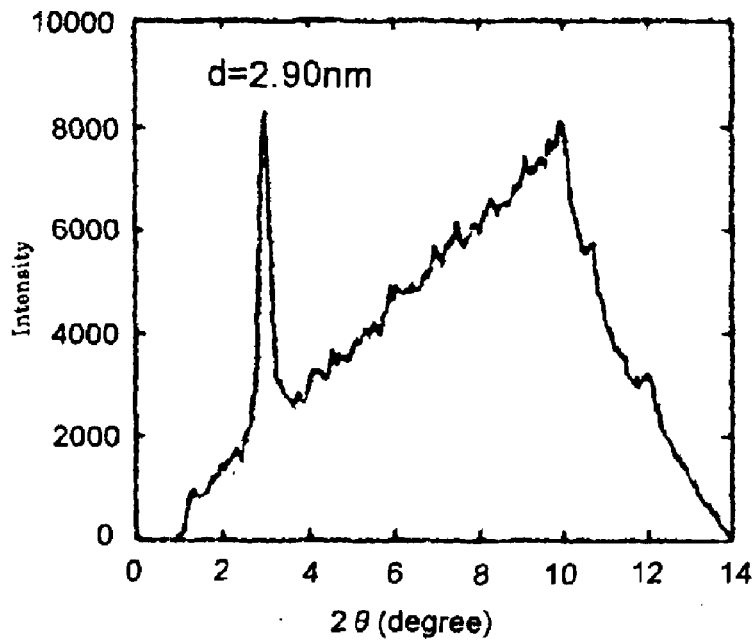
FIG. 6 is an XRD spectrum of an aqueous gel.

Recently, there have been several reports of X-ray crystallography techniques used to confirm molecular packing of the gelatinizer in the gel phase, and these are being used to clarify the gelatinizing mechanism of low molecular weight gelatinizers (Terech, P.; Weiss, R. G. Chem. Rev. 1997, 3313.: Hanabusa, K.; Matsumoto, M.; Kimura, M.; Kakehi, A.; Shirai, H. J. Colloid Interface Sci. 2000, 224, 231.: Abdallah, D. J.; Sirchio, S.; Weiss, R. G. Langmuir 2000, 16, 7558.: Sakurai, K.; Ono, Y.; Jung, J. H.; Okamoto, S.; Sakurai, S.; Shinkai, S. J. Chem. Soc., Perkin Trans. 2 2001, 108.). However, the relation between the molecular packing and physical gelatinizing properties of the gelatinizer molecules is still not well understood. The xerogel of this invention obtained from water by a freezing method gives a sponge-like aggregate, and it is not a typical crystal. From X-ray diffraction of the xerogel, the Inventors obtained information regarding the type of molecular packing of the gelatinizer molecules in an ordered gel. The diffraction pattern of the xerogel of this invention shows a periodic diffraction peak (FIG. 5), and shows that this xerogel is actually aggregated in a lamellar structure. The intervals (d) of the aggregate obtained by the XRD method are approximately 2.90 nanometers, 1.46 nanometers and 0.97 nanometers. These are almost precisely in a ratio of 1:1/2:1/3, are shorter than twice the molecular length of the gelatinizer (according to the CPK molecular model, 2.45 nanometers), and longer than one molecule. The peak at 2.90 nanometers observed in the xerogel, was observed also in the gel state (FIG. 6). These results strongly suggest that the aqueous gel of this invention has a bimolecular interdigitation film structure having a molecular film corresponding to the (100)

Figure 7:
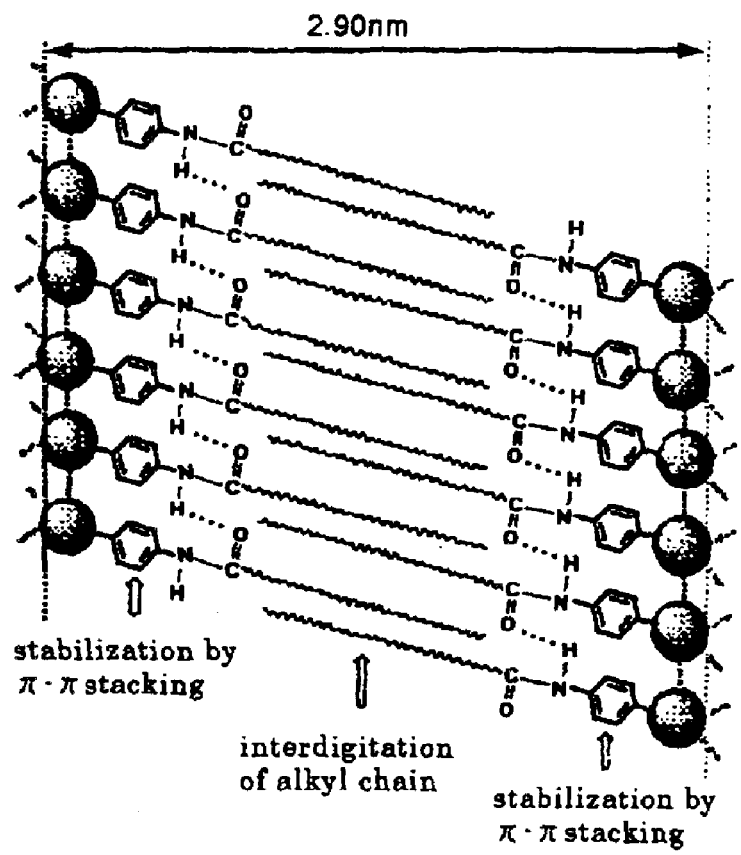
FIG. 7 is a diagram showing the autocoagulation of an aqueous gel.

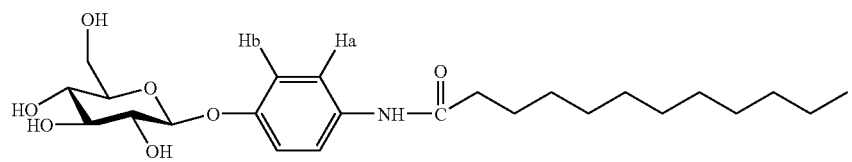

plane of thickness 2.90 nanometers (FIG. 7). Further, the wide angle X-ray diagram of the aqueous gel of this invention shows a series of sharp reflection peaks, which supports the hypothetical viewpoint that a regular lamellar high density packing is formed due to the interdigitation of hydrophobic interactions. This is the first example where a well-ordered two molecule layer forms an aqueous gel. From the results of XRD, FT-NMR and FT-IR, it is seen that the aqueous gel of this invention is stabilized by a combination of hydrogen bonds, π—π interactions and hydrophobic forces.

What is claimed is:

1. A hydrogelatinizer represented by:

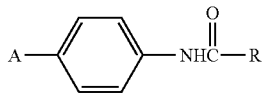

where, A is a sugar residue obtained by removing a hydrogen atoms from a ring hydroxyl group of glucopyranose or galactopyranose and R is an alkyl group.

2. The hydrogelatinizer according to claim 1, wherein R is a straight chain alkyl group having 6–20 carbon atoms.

3. The hydrogelatinizer according to claim 1, wherein R is a straight chain alkyl group having 10–20 carbon atoms.

4. A hydrogel comprising water and the hydrogelatinizer of claim 1 in an amount sufficient to form the hydrogel.

5. The hydrogel of claim 4 wherein R is a straight chain alkyl group having 6–20 carbon atoms.

6. The hydrogel of claim 5 wherein R is a straight chain alkyl group having 10–20 carbon atoms.

7. A method for producing a hydrogel comprising the steps of mixing a liquid and the hydrogelatinizer of claim 1, heating the mixture until the hydrogelatinizer dissolves, and cooling said mixture, wherein the liquid is water, a mixture of water and up to 1 wt % of methanol and ethanol, 1-butanol, t-butanol, tetrahydrofuran, chloroform, dichloromethane, n-hexane, ethyl acetate, dimethylformamide or dimethyl sulfoxide.

8. A hydrogel comprising a liquid and a hydrogelatinizer in an amount sufficient to form the hydrogel, wherein the hydrogelatinizer is represented by

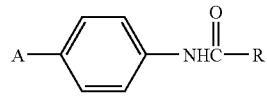

where A is a sugar residue and R is an alkyl group and wherein said liquid is water, a mixture of water and up to 1 wt % of methanol and ethanol, 1-butanol, t-butanol, tetrahydrofuran, chloroform, dichloromethane, n-hexane, ethyl acetate, dimethylformamide or dimethyl sulfoxide.

9. The hydrogel of claim 8 wherein A is a sugar residue obtained by removing a hydrogen atom from a ring hydroxyl group of an aldopyranose.

10. The hydrogel of claim 9 wherein said aldopyranose is glucopyranose or galactopyranose.

11. The hydrogel of claim 10 wherein R is a straight chain alkyl group having 6–20 carbon atoms.

12. The hydrogel of claim 11 wherein R is a straight chain alkyl group having 10–20 carbon atoms.

* * * * *